Figure 1:
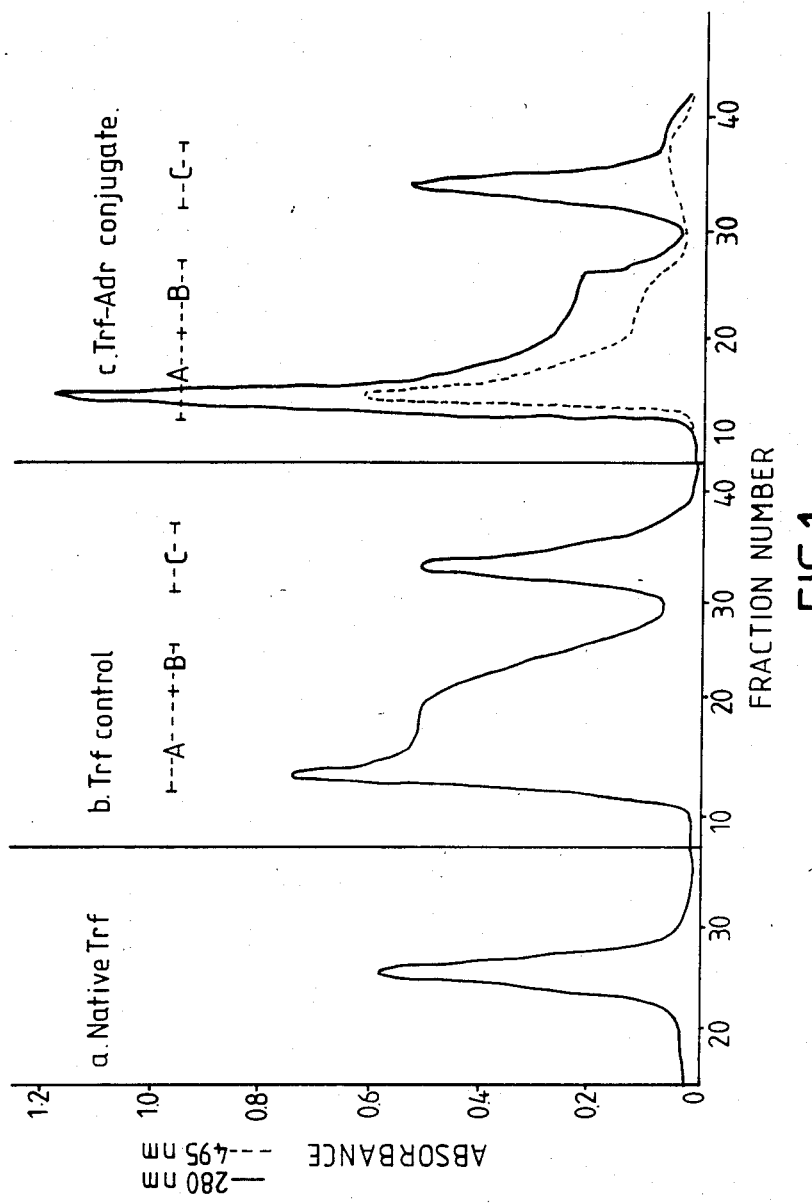

United States Patent [19]

Faulk

[11] Patent Number: 4,886,780

[45] Date of Patent: Dec. 12, 1989

[54] CONJUGATES OF APOTRANSFERRIN PROTEINS WITH ANTI-TUMOR AGENTS

[76] Inventor: Ward P. Faulk, Apsley, Hasliberg/Goldern CH-6085, Switzerland

[21] Appl. No.: 220,359

[22] Filed: Jul. 12, 1988

Related U.S. Application Data

[63] Continuation of Ser. No. 930,978, Nov. 13, 1986, which is a continuation of Ser. No. 719,275, filed as PCT GB83/00200 on Aug. 10, 1983, published as WO85/00812 on Feb. 28, 1985.

[51] Int. Cl.[4] .................. A61K 37/14; A61K 39/385; A61K 37/02; C07K 15/14
[52] U.S. Cl. ....................................... 514/8; 424/101; 514/21; 530/380; 530/389; 530/391; 530/406; 530/410; 530/807; 530/828; 530/394; 530/392; 436/529
[58] Field of Search ............... 530/380, 389, 391, 406, 530/410, 807, 828, 392, 394; 514/21, 8; 424/101

[56] References Cited

U.S. PATENT DOCUMENTS

| | | |
|---|---|---|
| 3,939,258 | 2/1976 | Niemann . |
| 4,046,722 | 9/1977 | Rowland ..................... 260/121 X |
| 4,174,384 | 11/1979 | Ullman et al. .............. 260/112 R X |
| 4,256,632 | 3/1981 | Levin et al. ................. 260/112.5 R |
| 4,320,109 | 3/1982 | Nakamura et al. . |
| 4,332,785 | 5/1982 | Allen et al. . |
| 4,376,765 | 3/1983 | Trouet et al. ............ 260/112.5 R X |
| 4,378,428 | 3/1983 | Farina et al. ................ 260/112 R X |
| 4,434,156 | 2/1984 | Trowbridge . |
| 4,447,547 | 5/1984 | Allen et al. . |
| 4,448,762 | 5/1984 | Richards et al. . |
| 4,448,763 | 5/1984 | Triplett . |
| 4,460,561 | 7/1984 | Goldenberg ................ 260/112 R X |
| 4,493,793 | 1/1985 | Chu ................................. 530/380 X |
| 4,522,750 | 6/1985 | Ades et al. ........................ 530/397 |
| 4,590,001 | 5/1986 | Stjernholm ....................... 530/394 |

FOREIGN PATENT DOCUMENTS

| | | |
|---|---|---|
| 2108528 | 9/1972 | Fed. Rep. of Germany . |
| 2150000 | 4/1973 | Fed. Rep. of Germany . |

OTHER PUBLICATIONS

The Lancet, Aug. 23, 1980, Faulk et al, 390–392.
Makromol. Chem. Suppl. 207–214 (1979), Wilchek.
Nature, 294 (1981), 171–173, Trowbridge et al.

*Primary Examiner*—Howard E. Schain
*Attorney, Agent, or Firm*—Armstrong, Nikaido, Marmelstein, Kubovcik & Murray

[57] ABSTRACT

Conjugates of transferrin or ceruloplasmin with anti-tumor agents. Such conjugates are useful in the treatment of tumors. Suitable anti-tumor agents include adriamycin, daunomycin, methotrexate, vincristin, 6-mercaptopurine, cytosine arabinoside and cyclophosphamide. Transferrin or ceruloplasmin is preferably coupled to the anti-tumor agent by means of glutaraldehyde.

3 Claims, 3 Drawing Sheets

CONJUGATES OF APOTRANSFERRIN PROTEINS WITH ANTI-TUMOR AGENTS

This application is a continuation of application Ser. No. 930,978 filed Nov. 13, 1986, which was a continuation of application Ser. No. 719,275 filed as PCT GB83/00200 on Aug. 10, 1983, published as WO85/00812 on Feb. 28, 1985, now abandoned.

This invention relates to conjugates of proteins with anti-tumour agents, and more particularly to conjugates of transferrin or ceruloplasmin with anti-tumour agents. The invention also relates to methods for preparing such conjugates.

Transferrin is a protein which occurs in blood plasma, including human blood plasma, and which has an important function in the transport of iron. The role of transferrin in heme synthesis in developing red blood cells has been widely studied, and the presence of transferrin receptors on reticulocytes has been noted.

Ceruloplasmin is a copper-binding glycoprotein which also occurs in blood plasma. It has been suggested that modified ceruloplasmin might fit into transferrin receptors.

It has been noted recently that transferrin receptors are to be found on the surfaces of tumour cells. It has been suggested that research into breast cancer therapy might be approached through the use of transferrin labelled with cytotoxic agents (Faulk et al. The Lancet, Aug. 23, 1980, page 392).

A favoured approach to producing tumour-specific drugs has involved the linking of cytostatic drugs such as daunomycin, adriamycin and methotrexate, to antibodies against tumour-associated surface antigens. The ability of such complexes to kill malignant cells selectively has, so far, been limited. An alternative, and more recent approach has been to link a toxin, instead of a cytostatic drug, to the antibody.

Following the identification of transferrin receptors on the surfaces of tumour cells by Faulk and Galbraith (Proc. Roy. Soc. (B) 204: 83-97, 1979), Trowbridge and Domingo (Nature, Vol. 294, page 171, 1981) have obtained monoclonal antibodies against the transferrin receptor of human cells, and have coupled such antibodies to ricin or diphtheria (toxin sub-units. They found that the growth of human tumour cells was specifically inhibited in vitro by such conjugates. However, in experiments designed to test the effectiveness of the antibody-toxin conjugates in vivo, they found that anti-transferrin receptor antibody alone inhibits the growth of human melanoma cells in nude mice. Indeed, they found no evidence that the conjugate is more effective than unmodified antibody in inhibiting growth of M21 melanoma cells in nude mice. That is to say, the cytotoxic properties of the ricin A moiety of the antibody-toxin conjugate were not manifest in vivo.

In surprising contrast to the results of Trowbridge and Domingo, it has now been found that when an anti-tumour agent is conjugated with transferrin or ceruloplasmin, not only does the protein moiety retain its affinity for transferrin receptors, but, moreover, the anti-tumour agent retains its anti-tumour properties.

According to the present invention, there is provided a conjugate of transferrin or ceruloplasmin with an anti-tumour agent. Preferably, the anti-tumour agent is adriamycin, methotrexate, vincristin, daunomycin, 6-mercaptopurine, cytosine arabinoside, or cyclo phosphamide. More preferably, the anti-tumour agent is adriamycin, and the protein with which it is conjugated is preferably apotransferrin.

It is particularly preferred that the transferrin or ceruloplasmin be linked to the anti-tumour agent by means of glutaraldehyde.

The transferrin or ceruloplasmin is preferably of human origin, though any transferrin or ceruloplasmin may be used which can bind to transferrin receptors on the surface of the tumour cell which it is desired to treat.

Preferably, the transferrin or ceruloplasmin conjugate is separated from conjugates which comprise aggregated transferrin or ceruloplasmin molecules and/or fragments of transferrin or ceruloplasmin molecules cross-linked by glutaraldehyde. Such aggregates and/or fragments may be separated from the desired conjugates by, for example, gel filtration chromatography.

Also provided by the present invention are conjugates of transferrin or ceruloplasmin as described above, for use in the treatment of tumours.

According to a further aspect of the present invention, there is provided a reagent kit for the treatment of tumours, comprising iron-bearing transferrin and a conjugate of transferrin or ceruloplasmin with an anti-tumour agent. Such of the patient's normal cells which have transferrin receptors may be protected against the effects of the conjugate by saturating these receptors with the iron-bearing transferrin before aadministration of the conjugate.

The present invention also provides a process for determining the susceptibility of tumour cells to anti-tumour agents, comprising administering separately to portions of said tumour cells conjugates of transferrin with a number of different anti-tumour agents. A reagent kit comprising a number of such different conjugates may be provided for this purpose.

It has been found that the conjugates of the present invention are taken up extremely rapidly by tumour cells. This means that within a matter of hours of removal from the patient, tumour cells may be tested against a range of conjugates of transferrin or ceruloplasmin with different anti-tumour agents. Such a process would enable the chemotherapy which is most effective for a given patient to be determined as soon as possible after isolation of the tumour cells.

Figure 2:
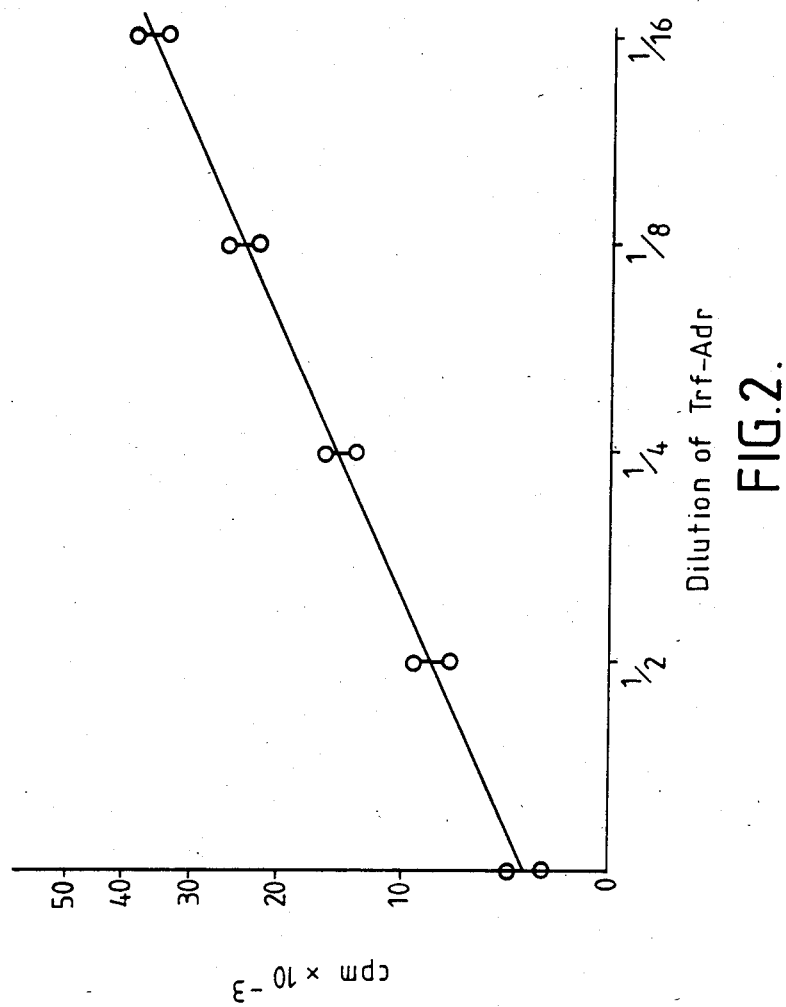
Figure 3:
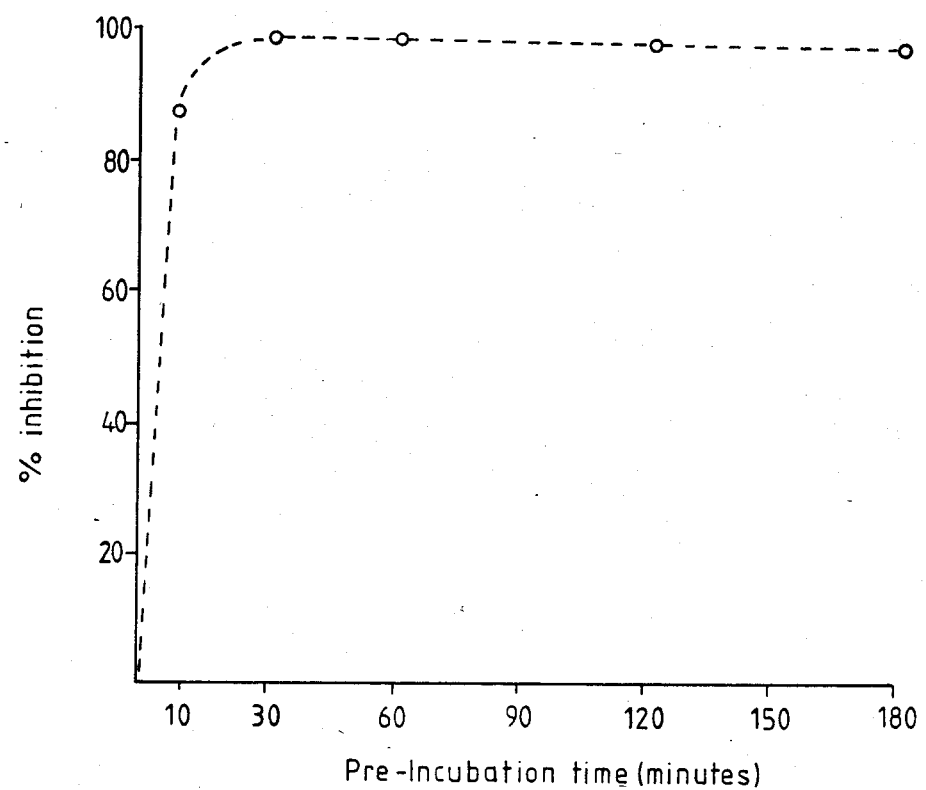

There are now described, by way of example, conjugates of transferrin and ceruloplasmin according to the present invention, and a method for preparing the same, with reference to the accompanying drawings, in which:

FIG. 1a shows the results of gel filtration chromatography of native transferrin, FIG. 1b shows the results of similar gel filtration chromatography of a transferrin control, FIG. 1c shows the results of simlar gel filtration chromatography of a transferrin-adriamycin conjugate according to the invention, FIG. 2 is a graph showing the effects of different quantities of conjugate on tumour cells, and FIG. 3 is a graph showing the time-course of $^3$H-thymidine uptake inhibition by conjugate.

EXAMPLE

Cells HL-60 (acute promyelocytic leukemia) and Daudi (Burkitt's lymphoma) cells, were grown in suspension at 37° C. in RPMI-1640 medium with L-glutamine, 25mM HEPES (Gibco European, Glasgow, Scotland), 50 mcg/ml gentamicin (Flow Laboratories, Ayrshire, Scotland) and supplemented with 10% fetal calf serum (Sera-Lab Ltd., Crawley Down, Sussex, England), this combination being hereafter referred to as complete medium. Human venous blood was collected into acid citrate dextrose solution, and peripheral blood mononuclear cells (PBM) were separated from venous blood samples with the use of Isolymph (Gallard-Schlesinger Chemical Mfg. Corp., Carle Place, New York, USA). Viability was determined by trypan blue exclusion.

Preparation of Conjugates

To a solution containing 10 mg of either human transferrin (Trf) (99% iron-free, from Behringwerke AG, Marburg, W. Germany) or human ceruloplasmin (Cer) (prepared as described by Pegandier, Z. et al, Clin. Chem. Acta 30, 387–394 (1970)), and 3 mg of adriamycin (Adr) hydrochloride (Farmitalia Co., Milan, Italy) in 1 ml of 0.1M phosphate buffered saline (PBS), pH 7.0 was added dropwise to 0.5 ml of an aqueous solution of 0.25% glutaraldehyde (BDH Chemicals Ltd., Poole, England) at room temperature (RT) with gentle mixing. After 2 hours incubation at RT in the dark, 0.5 ml of 1M ethanolamine (Sigma London Chemical Co. Ltd., Poole), pH 7.4., was added and incubated at 4° C. overnight. The mixture was then centrifuged at 1,000g for 15 minutes and the supernatant was collected and chromatographed through a column (2 cm×20 cm) of Sepharose CL-6B (Pharmacia Fine Chemicals, Uppsala, Sweden) equilibrated in 0.15M PBS, pH 7.2. Protein and Adr were identified as they emerged from the column by spectrophotometric readings taken at $OD_{280}$ for Trf or Cer and at $OD_{495}$ for Adr, respectively. Spectrophotometrically defined 1.2 ml fractions were pooled and sterilized by irradiation in a Gamma Cell 1000 irradiator (Atomic Energy of Canada) and stored at 4° C. in the dark until used.

Immunocytology and Fluorescence Localization of Trf and Adr.

Cells ($1\times10^6$) were reacted with 100 µl of Adr, Trf or Trf-Adr conjugate for 20 minutes at 4° C. or for 3 hours at 37° C., washed twice in Hank's balanced salt solution (HBSS, Gibco Europe) at 4° C. and reacted with 100 µl of a 1:20 dilution of a fluorescein isothiocyanate (FITC) conjugate of goat anti-human Trf (Atlantic Antibodies, Maine, USA). This antibody did not react with Daudi or HL-60 cells prior to their exposure to human Trf. Following incubation with anti-Trf, the cells were washed three times in HBSS at 4° C., suspended in 50% glycerol/PBS and mounted on glass slides to be studied by epiillumination with a Zeiss Universal microscope fitted with an HB 50 mercury arc lamp. This microscope was equipped with three different optical systems for the analysis of Trf and Adr:

(a) the FITC labelled anti-Trf could be identified by using a blue interference filter (BP455-490) with a FT510 chromatic beam splitter and a BP520-560 barrier filter; (b) Adr was identified by using a green interference filter (BP546/7) with a FT 580 chromatic beam splitter and a LP590 barrier filter; and (c) anti-Trf and Adr could be simultaneously identified by using a (BP455-490) interference filter, a FT510 chromatic beam splitter and a LP 520 barrier filter.

Measurements of Cellular Proliferation and Viability

For a direct inhibition assay, cells ($0.5\times10^6$) were incubated with 100 µl of sterile Trf-Adr or with Cer-Adr conjugates containing 1 µg of Adr, or with complete medium at 37° C. in 5% $CO_2$/air for 3 hours, following which they were washed twice incomplete medium for 7 minutes per wash at 4° C., and centrifuged at 400g. For a competitive inhibition assay, cells ($0.5\times10^6$) were incubated with or without 100 µl of Trf (1mg/ml) at 4° C. for 30 minutes, followed by incubation with Trf-Adr, Cer-Adr or PBS at 4° C. for 30 minutes. They were then washed twice at 4° C. and further incubated at 37° C. for 2 hours. For the quantification of cellular proliferation, 300 µl of complete medium was added to the washed cell pellet, and the cells were resuspended and distributed in triplicate as 100 µl aliquots in flat-bottom microtiter plates (Flow Laboratories), each well of which was pre-loaded with 100 µl of complete medium and 25 µl of 2 µCi of $^3$H-thymidine (specific activity, 2 Ci/mmole, Radiochemical Center, Amersham, Bucks, England). Plates were then incubated at 37° C. in 5% $CO_2$/air for 16 hours, and the cells were harvested on glass fiber filters in a MASH II multiple harvester (Microbiological Associates, Walkersville, Md., USA). The amount of $^3$H-thymidine incorporated into DNA was measured in a LKB 1216 Rackbeta II liquid scintillation counter and expressed as counts per minute (cpm). Quantitative measures of the viability and number of cells were also done in all experiments.

Chromatographic Properties of Trf, Trf-Adr Conjugates and Adr.

In preparing the conjugates, it was found that native Trf (1 ml of 5mg/ml in PBS) consistently emerged from a column of Sepharose CL-6B between fractions 22 and 30, peaking at fraction 26 (FIG. 1a). However, when Trf, which had been carried through the conjugation procedure in the absence of Adr, was chromatographed on the same column, a more complex pattern was obtained (FIG. 1b). The macromolecular peak (A in FIG. 1b) was precipitated by anti-Trf antibody in Ouchterlony and immunoelectrophoresis gels, as did the samples which emerged at the same place as native Trf, i.e., between fraction numbers 20–26 (B in FIG. 1b), but the late appearing peak (C in FIG. 1b) was not precipitated by anti-Trf in gels. It was therefore considered that "A" was Trf aggregates, "B" was chromatographically and antigenically native Trf and "C" was Trf fragments. When Trf-Adr conjugates were passed through the column, the $OD_{280}$ tracing was similar to the controls, but reading at $OD_{495}$ revealed Adr in both peaks A and B (FIG. 1c), whereas nothing was detected in $OD_{495}$ in the absence of Adr. Accordingly, peak B was used as Trf-Adr conjugate in the following experiments. It should be noted that Adr has a molecular weight of 579, and that it does not chromatograph within the molecular weight range of Sepharose CL-6B.

Immunological Identification of Trf on Plasma Membranes and Fluorescence Localization of Adr in Nuclei.

Trf, Adr and Trf-Adr conjugates were investigated for their ability to be bound by plasma membrane receptors and to intercalate with nuclear DNA. This was done by using two different manipulations; the first being the incubation of Trf-receptor-positive cells with the above reagents for 20 minutes at 4° C., and the second being incubation of cells with the same reagents for 3 hours at 37° C. For these experiments, Daudi and HL-60 cells were used, since it has previously been reported that their plasma membranes have receptors for Trf, and PBM were used at Trf receptor-negative cells. When HL-60 or Daudi cells were incubated with Trf which had been carried through the conjugation and chromatography in the absence of Adr, or with Trf-Adr conjugates for 20 minutes at 4° C., a uniformly speckled pattern of fluorescence could be identified on their plasma membranes following incubation with FITC labelled antibodies to human Trf. In contrast, only 8% of PBM were found to find Trf or Trf-Adr conjugates, and none of the PBM, HL-60 or Daudi cells reacted with FITC anti-Trf after being incubated with Adr alone (Table 1). However, incubation of PBM, HL-60 or Daudi cells with free Adr for 20 minutes at 4° C. resulted in a red fluorescence of their nuclei, a result which was not obtained by incubation of any of the target cells with Trf or Trf-Adr conjugates for 20 minutes at 4° C.

When these experiments were repeated with the use of the same cells and the same reagents, but with the incubation time changed to 3 hours and the temperature changed to 37° C., the results were different. In the first instance, the pattern of immunofluorescence following incubation of HL-60 or Daudi cells with Trf or Trf-Adr conjugates was no longer homogeneous, but appeared to be clustered into islands of fluorescent patches on plasma membranes. The most striking difference found with these changed conditions of time and temperature for incubation was that obtained with the Trf-Adr conjugates, for Adr could now be identified in the nucleus.

Effects of Trf-Adr Conjugates on $^3$H-Thymidine Uptake and Viability of Cells.

It is thought that Adr acts by inserting itself between base pairs of DNA, resulting in an inhibition of DNA synthesis and eventual cell death, so the inhibition of $^3$H-thymidine uptake as well as trypan blue exclusion were chosen as measures of cellular proliferation and viability, respectively. Incubation of Trf-Adr conjugates for 3 hours at 37° C. with Daudi and HL-60 cells followed by two washes and a 16 hour culture period in tritiated thymidine had the striking effect of diminishing both proliferation and viability, whereas minimal effects were observed for both thymidine incorporation and viability when PBM were tested under the same conditions (Table 2). The Trf control manifested moderate suppression of Daudi and HL-60 cells and augmentation of PBM proliferation, while Trf-Adr conjugates consistently recorded more than 90% suppression of both cell lines in thirty experiments. Regarding the death of PBM, it should be pointed out that, unlike Daudi and HL-60, very few PBM were found to contain Adr in their nuclei, indicating that dead cells resulted as a consequence of manipulation in vitro.

In order to provide additional evidence for the specific inhibition of cellular proliferation by Trf-Adr conjugates, Cer-Adr conjugates were used as a protein control for Trf. The choice of Cer was predicated by the observation that other proteins such as human albumin, Gc and alpha fetal protein are immunologically cross reactive with unfolded Trf but not with Cer. Although Cer-Adr conjugates were found to kill target cells in vitro, when Trf-Adr or Cer-Adr conjugates were allowed to displace Trf, Trf-Adr conjugates were twice as efficient as Cer-Adr conjugates (Table 3). These findings confirm the suggestion that modified Cer might fit into Trf receptors, but they additionally show that Trf-Adr conjugates have a higher affinity than Cer-Adr conjugates for Trf receptors. Native Trf alone in the growth media could not have been solely responsible for these results, since test and control experiments contained the same amount of Trf (Table 3).

Dose and Time Variables in Cell Killing by Trf-Adr Conjugates.

Trf-Adr conjugates were serially diluted to test the end-point of their ability to inhibit the uptake of $^3$H-thymidine. The results of these experiments showed that the proliferation of HL-60 cells was directly associated with the amount of Trf-Adr conjugate used in the initial 3 hour preincubation step of the assay (FIG. 3). Conjugate binding was rapid and achieved a plateau at 30 minutes preincubation (FIG. 4), although the in vitro assay for inhibition of cellular proliferation employed a preincubation step that was studied by using a fixed amount of conjugate with varied periods of time.

Effects of $^3$H-Thymidine Uptake of Leukemic Cells

Using techniques similar to those described in relation to Table 2 the effect of Trf-Adr on $^3$H-thymidine uptake by leukemic cells taken from six different patients suffering variously from acute myelocytic leukemia (AML) or from acute lymphatic leukemia (ALL) were studied. The results are set out in Table 4. Significant inhibition was noted in each case.

Trf Binding by PBM from Normals and Patients

Experiments were carried out to test the ability to bind transferrin of cells taken from a number of healthy people as well as from a number of patients with a lymphoma or a myeloma or suffering from AML, ALL, chronic myelocytic leukemia (CML), or chronic lymphatic leukemia (CML). Some of these patients were in remission (R) whilst others were not in remission (NR). In these experiments the technique used was generally as described above in relation to Table 1. The results are summarised in Table 5.

In vivo Tests of the Effects of Trf-Adr Treatment in Peripheral Blood of AML Patients.

Table 6 summarises the effects on a number of patients of treatment with 1 mg. Trf-Adr administered by the intravenous route in the form of conjugate in physiological saline. Patients Nos. 1, 4 and 5 were the same patients as are referred to in Table 4. The effects of this dosage on the counts of both blasts and polymorphonucleated neutrophiles (PMN) are listed.

TABLE 1

Plasma Membrane and Nuclear Reactivity of Trf, Adr and Trf—Adr Conjugates with HL-60 Cells at Different Temperatures and Times of Incubation

| Reagents | Temperature | Time | Membrane fluorescence for Trf | Nuclear Fluorescence for Adr |
|---|---|---|---|---|
| Trf | 4° C. | 20 minutes | 70–80/3+[1] | 0 |
| Adr | 4° C. | 20 minutes | 0 | 100[2] |
| Trf—Adr | 4° C. | 20 minutes | 70–80/3+ | 0 |
| Trf | 37° C. | 3 hours | 70–80/3+ | 0 |
| Adr | 37° C. | 3 hours | 0 | 100 |
| Trf—Adr | 37° C. | 3 hours | 70–80/3+ | 70–80 |

[1]Percentage of cells fluorescing/intensity of fluorescence.
[2]Percentage of positive cells.

TABLE 2

Effects of Trf—Adr on $^3$H—Thymidine Uptake and Viability of Cells

| | $^3$H—thymidine uptake (cpm) | | | Viability (%) | | |
|---|---|---|---|---|---|---|
| Cells | Control | Trf Control | Trf—Adr | Control | Trf Control | Trf—Adr |
| Daudi | 155,511.33 ± 6,793.22* | 72,339.66 ± 3,159.67 | 14,850.00 ± 812.43 | 89 | 73 | 63 |
| HL-60 | 199,918.66 ± 7489.50 | 32,058.33 ± 1,899.52 | 3,515.00 ± 124.65 | 92 | 88 | 56 |

TABLE 2-continued

Effects of Trf—Adr on ³H—Thymidine Uptake and Viability of Cells

| Cells | ³H—thymidine uptake (cpm) | | | Viability (%) | | |
|---|---|---|---|---|---|---|
| | Control | Trf Control | Trf—Adr | Control | Trf Control | Trf—Adr |
| PBM | 316.33 ± 87.61 | 672.67 ± 215.42 | 98.67 ± 25.01 | 94 | 87 | 86 |

*Mean ± SEM from data of triplicate cultures obtained from 30 experiments. Cells (0.5 × 10⁶) were incubated with growth medium (control), Trf control (B in FIG. 1b) or Trf—Adr (B in FIG. 1c) for 3 hours at 37° C., washed and incubated with ³H—thymidine for 16 hours at 37° C., after which the uptake of ³H—thymidine and viability were determined.
Discordance between the effects of Trf on thymidine incorporation and cell viability is explained by the mechanism of intercalation of Adr within DNA which blocks proliferation many hours before cell death ensues.

TABLE 3

Competitive Inhibition of Trf—Adr and Cer—Adr with Trf on ³H—thymidine Uptake of Daudi Cells

| Reagent | Condition | |
|---|---|---|
| | No preincubation | Preincubation with Trf |
| Trf—Adr | 87000.67 ± 5857.78 | 48624.33 ± 3724.19 |
| Cer—Adr | 80687.33 ± 2025.06 | 85563.33 ± 5677.34 |
| Control | 145987.00 ± 6266.32 | 122467.33 ± 7625.16 |

Cells were preincubated with or without 100 μl of Trf for 30 minutes at 4° C., followed by incubation with Trf—Adr, Cer—Adr or PBS for 30 minutes at 4° C., washed twice at 4° C., then further incubated for 2 hours at 37° C. The measurement of incorporation of ³H—thymidine was as detailed in materials and methods.

TABLE 4

Effects of Trf—Adr on ³H—thymidine Uptake of Leukemic Cells

| Cells | ³H—thymidine uptake (cpm) | | Inhibition (%) |
|---|---|---|---|
| | Control | Trf—Adr | |
| Patient No. 1 (AML) | | | |
| PBM | 6,259 ± 357 | 75 ± 22 ° | 98.8 |
| Marrow | 4,747 ± 821 | 1,334 ± 57 | 71.9 |
| Patient No. 2 (AML) | | | |
| PBM | 1,582 ± 59 | 238 ± 15 | 85.0 |
| Marrow | 5,733 ± 219 | 657 ± 286 | 88.5 |
| Patient No. 3 (ALL) | | | |
| PBM | 412 ± 72 | 186 ± 34 | 54.9 |
| Marrow | 1,659 ± 56 | 923 ± 79 | 44.4 |
| Patient No. 4 (AML) | | | |
| PBM | 5,426 ± 242 | 1,995 ± 173 | 63.3 |
| Marrow | 23,972 ± 2,183 | 3,845 ± 256 | 84.0 |
| Patient No. 5 (AML) | | | |
| PBM | 3,451 ± 88 | 597 ± 38 | 82.8 |
| Marrow | 14,836 ± 957 | 1,894 ± 91 | 87.2 |
| Patient No. 6 (Anemia/AML) | | | |
| PBM | 1,475 ± 100 | 449 ± 108 | 69.5 |
| Marrow | 46,974 ± 4,836 | 17,208 ± 819 | 63.4 |

TABLE 5

Trf Binding by PBM from Normals and Patients

| Diagnosis | No. of cases | Anti—Trf (%) | Trf + Anti—Trf (%) |
|---|---|---|---|
| Normal | 23 | 2.83 ± 3.02 | 8.30 ± 3.55 |
| Lymphoma | 18 | 14.72 ± 14.00 | 30.44 ± 14.96 |
| Myeloma | 7 | 15.28 ± 9.21 | 23.71 ± 7.65 |
| AML (R) | 6 | 9.33 ± 3.33 | 18.17 ± 5.56 |
| AML (NR) | 1 | 65.00 ± 0.00 | 81.00 ± 0.00 |
| CML | 6 | 10.83 ± 9.66 | 20.50 ± 7.76 |
| CLL | 10 | 6.10 ± 4.48 | 14.80 ± 7.24 |

TABLE 6

Effects of Trf—Adr Treatment in Peripheral Blood of AML Patients

| Patient No. | Sex | Age | Blasts (%) | | PMN (%) | |
|---|---|---|---|---|---|---|
| | | | before | after | before | after |
| 1 | M | 20 | 76 | 30 | 8 | 46 |
| 4 | M | 73 | 98 | 93 | 1 | 2 |
| 5 | M | 49 | 74 | 72 | 5 | 15 |
| 7 | F | 28 | 22 | 0 | 18 | 36 |

I claim:

1. A conjugate of apotransferrin conjugated to adriamycin by glutaraldehyde.

2. Conjugate of claim 1, wherein said apotransferrin is human apotransferrin.

3. A method of treating a subject having a leukemia susceptible to adriamycin therapy, said method comprising administering to said patient an anti-tumor effective amount of the conjugate of claim 1.

* * * * *